(12) United States Patent
Thorpe et al.

(10) Patent No.: US 11,684,336 B2
(45) Date of Patent: Jun. 27, 2023

(54) SYSTEMS AND METHODS FOR DETECTING NEUROLOGICAL CONDITIONS

(71) Applicant: NovaSignal Corp., Los Angeles, CA (US)

(72) Inventors: Samuel G. Thorpe, Los Angeles, CA (US); Corey M. Thibeault, Los Angeles, CA (US); Nicolas Canac, Los Angeles, CA (US); Michael O'Brien, Los Angeles, CA (US)

(73) Assignee: NovaSignal Corp., Los Angeles, CA (US)

( * ) Notice: Subject to any disclaimer, the term of this patent is extended or adjusted under 35 U.S.C. 154(b) by 0 days.

(21) Appl. No.: 17/486,300

(22) Filed: Sep. 27, 2021

(65) Prior Publication Data

US 2022/0008032 A1    Jan. 13, 2022

Related U.S. Application Data

(63) Continuation of application No. 16/254,416, filed on Jan. 22, 2019, now Pat. No. 11,129,587.

(Continued)

(51) Int. Cl.
*A61B 8/08* (2006.01)
*A61B 8/00* (2006.01)
(Continued)

(52) U.S. Cl.
CPC .......... *A61B 8/0808* (2013.01); *A61B 5/4076* (2013.01); *A61B 8/06* (2013.01);
(Continued)

(58) Field of Classification Search
None
See application file for complete search history.

(56) References Cited

U.S. PATENT DOCUMENTS 5,379,770 A    1/1995    Van Veen
8,075,485 B2   12/2011   Smith
(Continued)

FOREIGN PATENT DOCUMENTS

JP    2006-025904 A    2/2006
WO   WO-92/07515 A1    5/1992
(Continued)

OTHER PUBLICATIONS

Final Office Action dated Nov. 5, 2021, from U.S. Appl. No. 15/971,260.
(Continued)

*Primary Examiner* — Katherine L Fernandez
(74) *Attorney, Agent, or Firm* — Foley & Lardner LLP

(57) ABSTRACT

Systems, apparatuses, methods, and non-transitory computer-readable media related to a tool for determining presence or absence of a neurological condition in a subject are provided. The tool includes an ultrasound device configured to collect ultrasound data from a head of the subject. The tool further includes a processing circuit configured to calculate a curvature metric based on the ultrasound data. The processing circuit is further configured to calculate a velocity asymmetry metric based on the ultrasound data. The tool is further configured to determine presence or absence of the neurological condition in the subject based on the curvature metric and the velocity asymmetry metric.

20 Claims, 4 Drawing Sheets

Related U.S. Application Data

(60) Provisional application No. 62/728,624, filed on Sep. 7, 2018, provisional application No. 62/620,188, filed on Jan. 22, 2018.

(51) Int. Cl.
 *A61B 5/00* (2006.01)
 *A61B 8/06* (2006.01)

(52) U.S. Cl.
 CPC .......... *A61B 8/0891* (2013.01); *A61B 8/4488* (2013.01); *A61B 8/488* (2013.01); *A61B 8/5223* (2013.01); *A61B 8/565* (2013.01); *A61B 5/7203* (2013.01); *A61B 5/7225* (2013.01); *A61B 5/7264* (2013.01); *A61B 8/42* (2013.01); *A61B 8/4444* (2013.01)

(56) References Cited

U.S. PATENT DOCUMENTS

| | | |
|---|---|---|
| 2002/0177843 A1 | 11/2002 | Anderson et al. |
| 2003/0032869 A1 | 2/2003 | Muramatsu et al. |
| 2004/0243006 A1 | 12/2004 | Nakata et al. |
| 2004/0267120 A1 | 12/2004 | Podany et al. |
| 2005/0240102 A1 | 10/2005 | Rachlin et al. |
| 2005/0261582 A1 | 11/2005 | Becker et al. |
| 2006/0052704 A1 | 3/2006 | Baba et al. |
| 2006/0184034 A1 | 8/2006 | Haim et al. |
| 2008/0021318 A1 | 1/2008 | Kato et al. |
| 2008/0214939 A1 | 9/2008 | Harhen |
| 2008/0221452 A1 | 9/2008 | Njemanze |
| 2009/0076404 A1 | 3/2009 | Hopenfeld |
| 2009/0131805 A1 | 5/2009 | O'Brien et al. |
| 2010/0125213 A1 | 5/2010 | Lo et al. |
| 2010/0249598 A1 | 9/2010 | Smith et al. |
| 2011/0201961 A1 | 8/2011 | Hu et al. |
| 2012/0136255 A1 | 5/2012 | Fan et al. |
| 2012/0165675 A1 | 6/2012 | Syme |
| 2012/0265196 A1 | 10/2012 | Turner et al. |
| 2013/0095701 A1 | 4/2013 | Golko et al. |
| 2013/0245451 A1 | 9/2013 | Mochizuki et al. |
| 2014/0180128 A1 | 6/2014 | Corl |
| 2014/0343431 A1 | 11/2014 | Vajinepalli et al. |
| 2015/0025390 A1 | 1/2015 | Hewitt et al. |
| 2015/0208159 A1 | 7/2015 | Sander et al. |
| 2016/0256130 A1 | 9/2016 | Hamilton et al. |
| 2016/0278736 A1 | 9/2016 | Hamilton et al. |
| 2017/0086789 A1 | 3/2017 | Brandl et al. |
| 2017/0086792 A1 | 3/2017 | Chono |
| 2017/0188993 A1* | 7/2017 | Hamilton ............. A61B 8/5223 |
| 2017/0215811 A1 | 8/2017 | Newberry |
| 2018/0103862 A1 | 4/2018 | Kim |
| 2018/0240543 A1 | 8/2018 | Maeda et al. |
| 2019/0216433 A1* | 7/2019 | Hamilton ............. A61B 8/4281 |

FOREIGN PATENT DOCUMENTS

| | | |
|---|---|---|
| WO | WO-97/24986 A2 | 7/1997 |
| WO | WO-2008/091938 A1 | 7/2008 |
| WO | WO-2015/073903 A1 | 5/2015 |
| WO | WO-2016/171476 A1 | 10/2016 |

OTHER PUBLICATIONS

Chia-Chi Chang et al: "Quantitative Non-Stationary Assessment of Cerebral Hemodynamics by Empirical Mode Decomposition of Cerebral Doppler Flow Veolocity", Advances in Adaptive Data Analysis, vol. 05, No. 01, Jan. 1, 2013 (Jan. 1, 2013), p. 1350002, XP055510620, ISSN: 1793-5369, DOI: 10.1142/S1793536913500027.
Final Office Action dated Aug. 6, 2019, from U.S. Appl. No. 16/003,012.
Final Office Action dated Feb. 28, 2020, from U.S. Appl. No. 16/255,531.
Final Office Action dated Feb. 3, 2021, from U.S. Appl. No. 16/254,416.
Final Office Action dated Jan. 13, 2020, from U.S. Appl. No. 16/254,416.
Final Office Action dated Jan. 2, 2019, from U.S. Appl. No. 16/003,012.
Final Office Action dated Jun. 11, 2020, from U.S. Appl. No. 15/971,260.
Final Office Action dated Mar. 21, 2019, from U.S. Appl. No. 15/971,260.
International Preliminary Report on Patentability dated Jul. 30, 2020, from application No. PCT/US2018/031069.
International Search Report and Written Opinion dated Apr. 12, 2019, from application No. PCT/US2019/014802.
International Search Report and Written Opinion dated Mar. 27, 2019, from application No. PCT/US2019/014587.
International Search Report and Written Opinion dated Oct. 9, 2018, from application No. PCT/US2018/031069.
Moppet, et al. "Transcranial Doppler Ultrasonography in Anaesthesia and Intensive Care", British Journal of Anaesthesia 93 (5): 710-24, 2004.
Ni, et al., "Serial Transcranial Doppler Sonography in Ischemic Strokes in Middle Cerebral Artery Territory" Journal of Neuroimaging, Oct. 1, 1994, pp. 232-236.
Non-Final Office Action dated Aug. 22, 2019, from U.S. Appl. No. 16/255,531.
Non-Final Office Action dated Dec. 14, 2018, from U.S. Appl. No. 15/971,260.
Non-Final Office Action dated Feb. 4, 2021, from U.S. Appl. No. 15/971,260.
Non-Final Office Action dated Jul. 12, 2019, from U.S. Appl. No. 16/254,416.
Non-Final Office Action dated Jun. 9, 2020, from U.S. Appl. No. 16/254,416.
Non-Final Office Action dated Mar. 7, 2019, from U.S. Appl. No. 16/003,012.
Non-Final Office Action dated Oct. 30, 2019, from U.S. Appl. No. 15/971,260.
Non-Final Office Action dated Sep. 28, 2018, from U.S. Appl. No. 16/003,012.
Notice of Allowance dated Jul. 24, 2020, from U.S. Appl. No. 16/003,012.
Notice of Allowance dated May 24, 2021, from U.S. Appl. No. 16/254,416.
Purvis et al., Transcranial Doppler Investigation of Hemodynamic Alterations Associated with Blunt Cervical Vascular Injuries in Trauma Patients:, Journal of Ultrasound Medicine, vol. 32, pp. 1759-1768, 2013 (Year 2013).
Saqqur, et al., "Derivation of Power M-Mode Transcranial Doppler Criteria for Angiographic Proven MCA Occlusion", Journal of Neuroimaging, vol. 16, No. 4, Oct. 1, 2006, pp. 323-328.
Thorpe, et al., "Decision Criteria for Large Vessel Occlusion Using Transcranial Doppler Waveform Morphology", Frontiers in Neurology, vol. 9, Oct. 17, 2018.
Vaitkus P J et al: "Development of Methods to Analyse Transcranial Doppler Ultrasound Signals Recorded in Microgravity", Medical and Biological Engineering and Computing, Springer, Heildelberg, DE, vol. 28, No. 4, Jul. 1, 1990 (Jul. 1, 1990), pp. 306-311, XP000136091, ISSN: 0140-0018, DOI: 10.1007/BF02446147.
U.S. Non-Final Office Action dated May 26, 2022, from U.S. Appl. No. 15/971,260.
U.S. Final Office Action dated Nov. 30, 2022, from U.S. Appl. No. 15/971,260.
U.S. Non-Final Office Action dated Oct. 6, 2022, from U.S. Appl. No. 17/107,843.
Australian Re-examination Report dated Dec. 21, 2022, for application No. 2019210133.
U.S. Final Office Action dated Mar. 20, 2023, for U.S. Appl. No. 17/107,843.
U.S. Non-Final Office Action dated Apr. 12, 2023, for U.S. Appl. No. 15/971,260.

* cited by examiner

SYSTEMS AND METHODS FOR DETECTING NEUROLOGICAL CONDITIONS

CROSS-REFERENCE TO RELATED PATENT APPLICATIONS

The present application is a Continuation of U.S. patent application Ser. No. 16/254,416, filed on Jan. 22, 2019, which claims priority to, and the benefit of, U.S. provisional patent application Ser. No. 62/620,188, titled SYSTEMS AND METHODS FOR DIAGNOSING NEUROLOGICAL CONDITIONS, and filed on Jan. 22, 2018, which is incorporated herein by reference in its entirety. The present disclosure also claims priority to, and the benefit of, U.S. provisional patent application Ser. No. 62/728,624, titled DECISION CRITERIA FOR LARGE VESSEL OCCLUSION USING TRANSCRANIAL DOPPLER WAVEFORM MORPHOLOGY, and filed on Sep. 7, 2018, which is incorporated herein by reference in its entirety.

BACKGROUND

Early detection of neurological conditions, such as Large Vessel Occlusion (LVO) identification may be key to enabling rapid triage and transfer to appropriate care. Computed Tomography Angiography (CTA) is currently used for detecting neurological conditions, but is limited to in-hospital use. Current pre-hospital LVO assessment lack reliability due to training requirements and low inherent accuracies, causing delays in triage, transfer, and treatment. Ultrasound (e.g., transcranial Doppler (TCD) ultrasound) is a reliable diagnostic tool for assessing the presence and severity of LVO, and is non-invasive, inexpensive, and portable. However, a limiting factor is the TCD operator's ability to interpret collected ultrasound data (e.g., Cerebral Blood Flow Velocity (CBFV) waveforms). Such challenges have contributed to TCD being critically underutilized for LVO assessment.

SUMMARY

According to various arrangements, there is provided a tool for determining presence or absence of a neurological condition in a subject. The tool includes an ultrasound device configured to collect ultrasound data from a head of the subject. The tool further includes a processing circuit configured to calculate a curvature metric based on the ultrasound data. The processing circuit is further configured to calculate a velocity asymmetry metric based on the ultrasound data. The processing circuit is further configured to determine presence or absence of the neurological condition in the subject based on the curvature metric and the velocity asymmetry metric.

In some arrangements, the processing circuit is further configured to compare the curvature metric and the velocity asymmetry metric to a plurality of thresholds.

In some arrangements, values of the thresholds are configured to be increased or decreased by an operator of the tool.

In some arrangements, the plurality of thresholds include a minimum curvature threshold or a maximum curvature threshold and the processing circuit is further configured to compare the curvature metric to the minimum curvature threshold or the maximum curvature threshold.

In some arrangements, in response to determining that the curvature metric is less than the minimum curvature threshold, the processing circuit is configured to determine presence of the neurological condition.

In some arrangements, in response to determining that the curvature metric is greater than the maximum curvature threshold, the processing circuit is configured to determine absence of the neurological condition.

In some arrangements, the plurality of thresholds includes a velocity asymmetry threshold, and, in response to determining that the curvature metric is between the minimum curvature threshold and the maximum curvature threshold, the processing circuit is further configured to compare the velocity asymmetry metric to the velocity asymmetry threshold.

In some arrangements, in response to determining that the velocity asymmetry metric is less than the velocity asymmetry threshold, the processing circuit is configured to determine presence of the neurological condition.

In some arrangements, in response to determining that the velocity asymmetry metric is greater than the velocity asymmetry threshold, the processing circuit is configured to determine absence of the neurological condition.

In some arrangements, the ultrasound data includes a first blood flow waveform from a first anatomical portion of the head of the subject and a second blood flow waveform from a second anatomical portion of the head of the subject, the first anatomical portion different from the second anatomical portion.

In some arrangements, the first anatomical portion includes a first blood vessel of the head of the subject and the second anatomical portion comprises a second blood vessel of the head of the subject.

In some arrangements, the first blood vessel includes a right middle cerebral artery of the subject and the second blood vessel includes a left middle cerebral artery of the subject.

In some arrangements, the first and second blood flow waveforms includes cerebral blood flow velocity (CBFV) waveforms.

In some arrangements, the curvature metric quantifies a degree to which the first blood flow waveform and the second blood flow waveform deviate from a straight line.

In some arrangements, the velocity asymmetry metric quantifies a degree to which a first velocity of the first blood flow waveform differs from a second velocity of the second blood flow waveform.

In some arrangements, the processing circuit is configured to determine presence of the neurological condition in the subject based on the curvature metric first and then the velocity asymmetry metric second.

In some arrangements, the neurological condition includes Large Vessel Occlusion.

In some arrangements, the tool further includes a display and the processing circuit is further configured to display one or more indicators at the display representing the calculated curvature metric and the velocity asymmetry metric.

In some arrangements, the tool further includes a display and the processing circuit is further configured to display an indicator at the display indicating presence of the neurological condition.

According to various arrangements, there is provide a method for determining presence or absence of a neurological condition in a subject. The method includes collecting, by an ultrasound device, ultrasound data from a head of the subject. The method further includes calculating, by a processing circuit, a curvature metric based on the ultrasound data. The method further includes calculating, by the processing circuit, a velocity asymmetry metric based on the ultrasound data. The method further includes determining, by the processing circuit, presence or absence of the neurological condition in the subject based on the curvature metric and the velocity asymmetry metric.

According to various arrangements, there is provided a non-transitory processor-readable medium storing processor-readable instructions such that, when executed, causes a processor to determine presence or absence of a neurological condition by collecting ultrasound data from a head of the subject; calculating a curvature metric based on the ultrasound data; calculating a velocity asymmetry metric based on the ultrasound data; and determining presence or absence of the neurological condition in the subject based on the curvature metric and the velocity asymmetry metric.

BRIEF DESCRIPTION OF THE FIGURES

Features and aspects of the present disclosure will become apparent from the following description and the accompanying example arrangements shown in the drawings, which are briefly described below.

DETAILED DESCRIPTION

The detailed description set forth below in connection with the appended drawings is intended as a description of various configurations and is not intended to represent the only configurations in which the concepts described herein may be practiced. The detailed description includes specific details for providing a thorough understanding of various concepts. However, it will be apparent to those skilled in the art that these concepts may be practiced without these specific details. In some instances, well-known structures and components are shown in block diagram form in order to avoid obscuring such concepts.

In the following description of various arrangements, reference is made to the accompanying drawings which form a part hereof and in which are shown, by way of illustration, specific arrangements in which the arrangements may be practiced. It is to be understood that other arrangements may be utilized, and structural changes may be made without departing from the scope of the various arrangements disclosed in the present disclosure.

Arrangements described herein relate to apparatuses, systems, methods, and non-transitory computer-readable media for determining presence of neurological conditions, for example, Large Vessel Occlusion (LVO). For quantifying TCD waveform morphology for the purpose of LVO identification, a diagnostic biomarker measuring curvature of a blood flow velocity waveform has been recently proposed. Further disclosure regarding curvature can be found in non-provisional patent application Ser. No. 16/003,012, titled WAVEFORM VISUALIZATION TOOL FOR FACILITATING MEDICAL DIAGNOSIS, and filed on Jun. 7, 2018, which is incorporated herein by reference in its entirety.

In some arrangements, the curvature metric and a velocity asymmetry metric are both utilized for the detection of LVO in subjects, for example, by leveraging complementary information from both metrics. In some arrangements, a decision tree incorporating both metrics is implemented. Accordingly, in some arrangements, objective, intuitive, and easily communicated TCD-based decision criteria are provided, allowing physicians and first responders alike a common language for LVO assessment.

Figure 1:
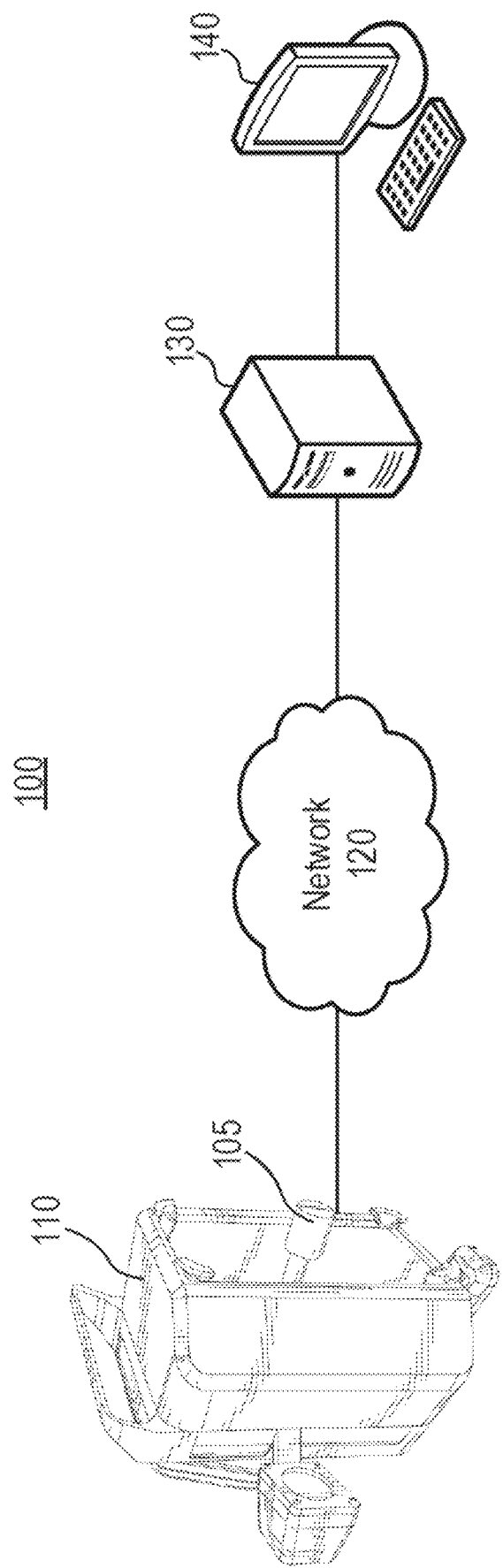
FIG. 1 is a schematic diagram illustrating a system for detecting neurological conditions according to various arrangements.

FIG. 1 is a schematic diagram illustrating a system 100 for detecting neurological conditions according to various arrangements. Referring to FIG. 1, the system 100 includes at least a device 110, a controller 130, and an output device 140.

In some examples, the device 110 is an ultrasound device (e.g., a TCD ultrasound device) configured to transmit and/or receive acoustic energy with respect to a head of a subject. The device 110 includes at least one transducer or probe 105 (e.g., at least one ultrasound probe) configured to transmit and/or receive ultrasound acoustic energy with respect to the head. For example, the probe 105 includes at least one TCD transducer. The probe 105 can be configured to collect the ultrasound data in the manner described to find a high-quality signal within a temporal window region (temple) of the head. In other arrangements, the probe 105 can be configured to collect the ultrasound data in the manner described to find a high quality signal within different acoustic windows such as but not limited to, a temporal window, a transorbital window, a suboccipital window, and so on. In some arrangements, the system 100 includes two devices 110, each device 110 including an ultrasound probe 105, which can be placed near or on the temporal window region on either side of the head (e.g., a first device 110 including a probe 105 at a first side of the head and a second device 110 including a probe 106 at a second side of the head that is opposite to the first side of the head). The probe 105 can be place and operated manually or robotically. A lubricating gel can be applied between the head and the probe 105 to improve acoustic transmission.

The controller 130 is configured to receive the ultrasound data collected and output by the device 110 and to perform signal processing for the ultrasound data. In that regard, the device 110 is operatively coupled to the controller 130 via a suitable network 120 to send the ultrasound data to the controller 130. The network 120 can be wired or wireless (e.g., 802.11X, ZigBee, Bluetooth®, Wi-Fi, or the like). The controller 130 is configured to assess signal quality of the ultrasound data in the manner described. In some examples, the controller 130 is further configured to perform signal processing functions such as but not limited to, beat segmentation, morphological feature identification, and so on to facilitate a physician, clinician, technician, or healthcare provider with diagnosis. Further, as described, the device 110 can automatically adjust or reposition the position and orientation of the probe 105 responsive to a determination that the probe 105 is not optimally placed. In other arrangements, a human operator can adjust and reposition the position and orientation of the probe 105. In some arrangements, the controller 130, the output device 140, and a portion of the network 120 are incorporated into a single device (e.g., a touchscreen tablet device). In some arrangements, the device 110 (and/or the other components such as but not limited to, the controller 130 and output device 140)

is powered by a wired connection. In other arrangements, the device 110 (and/or the other components 130 and 140) are powered wirelessly (e.g., by a portable battery).

In some arrangements, the output device 140 includes any suitable device configured to display information, results, messages, and the like to an operator (e.g., a physician, clinician, technician, or care provider) of the system 100. For example, the output device 140 includes but is not limited to, a monitor, a touchscreen, or any other output device configured to display the ultrasound data (e.g., cerebral blood flow velocity (CBFV) waveforms), morphology indicators corresponding to the ultrasound data, and so on for facilitating diagnosis.

In some examples, the detection of neurological conditions (e.g., LVO) can be used either in real-time (for real-time detection by, e.g., the device 110) or for post-processing (e.g., not in real-time but after signals have been collected from a subject for subsequent detection). With respect to real-time detection, data collected by the device 110 is collected and assessed using the detection criteria in real-time (e.g., as the data is received from the device 110 during a live scan).

With respect to post-processing detection, the data collected by the device 110 or another device similar to the device 110 can be stored in a database to be processed later. The data (e.g., signal segments) previously stored in the database can be subsequently evaluated (e.g., using the decision method described herein).

In some arrangements, the system 100 as described herein is used in conjunction with other diagnostic ultrasound procedures, such as, but not limited to, needle guidance, intravascular ultrasound (e.g., examination of vessels, blood flow characteristics, clot identification, emboli monitoring, and so on), echocardiograms, abdominal sonography (e.g., imaging of the pancreas, aorta, inferior vena cava, liver, gall bladder, bile ducts, kidneys, spleen, appendix, rectal area, and so on), gynecologic ultrasonography (e.g., examination of pelvic organs such as uterus, ovaries, Fallopian tubes, and so on), obstetrical sonography, otolaryngological sonography (e.g., imaging of the thyroid (such as for tumors and lesions), lymph nodes, salivary glands, and so on), neonatal sonography (e.g., assessment of intracerebral structural abnormalities through soft spots of a skull of an infant, bleeds, ventriculomegaly, hyrdrocephalus, anoxic insults, and so on), ophthamological procedures (e.g., A-scan ultrasound biometry, B-scan ultrasonography, and so on), pulmonological uses (e.g., endobronchial ultrasound (EBUS)), urological procedures (e.g., determination of an amount of fluid retained in a subject's bladder, imaging of pelvic organs (such as uterus, ovaries, urinary bladder, prostate, and testicles), and detection of kidney stones), scrotal sonography (e.g., to evaluate testicular pain, identify solid masses, and so on), musculoskeletal procedures (e.g., examination of tendons, muscles, nerves, ligaments, soft tissue masses, bone surfaces, and so on), bone fracture sonography, testing for myopathic disease, estimating lean body mass, proxy measures of muscle quality (e.g., tissue composition), nephrological procedures (e.g., renal ultrasonography), and the like.

In some arrangements, the system 100 as described herein is used in conjunction with therapeutic ultrasound procedures, such as, but not limited to, high-intensity focused ultrasound (HIFU), focused ultrasound surgery (FUS), Magnetic resonance-guided focused ultrasound (MRgFUS), lithotripsy (e.g., breaking up kidney stones, bezoars, gall stones, and the like), targeted ultrasound drug delivery, trans-dermal ultrasound drug delivery, ultrasound hemostasis, cancer therapy, ultrasound-assisted thrombolysis, dental hygiene (e.g., cleaning teeth), phacoemulsification, ablation (e.g., of tumors or other tissue), acoustic targeted drug delivery (ATDD), trigger release of drugs (e.g., anti-cancer drugs), ultrasound-guided treatments (sclerotherapy, endovenous laser treatment, liposuction, and so on), and the like. In some arrangements, ultrasound is used for physical therapy applications, including, but not limited to, stimulating tissue beneath the skin's surface (e.g., by using very high frequency sound waves, such as, as an example, between about 800,000 Hz and 2,000,000 Hz), treating musculoskeletal ailments with ultrasound exposure (e.g., ligament sprains, muscle strains, tendonitis, joint inflammation, plantar fasciitis, metatarsalgia, facet irritation, impingement syndrome, bursitis, rheumatoid arthritis, osteoarthritis, and scar tissue adhesion), and the like.

Figure 2:
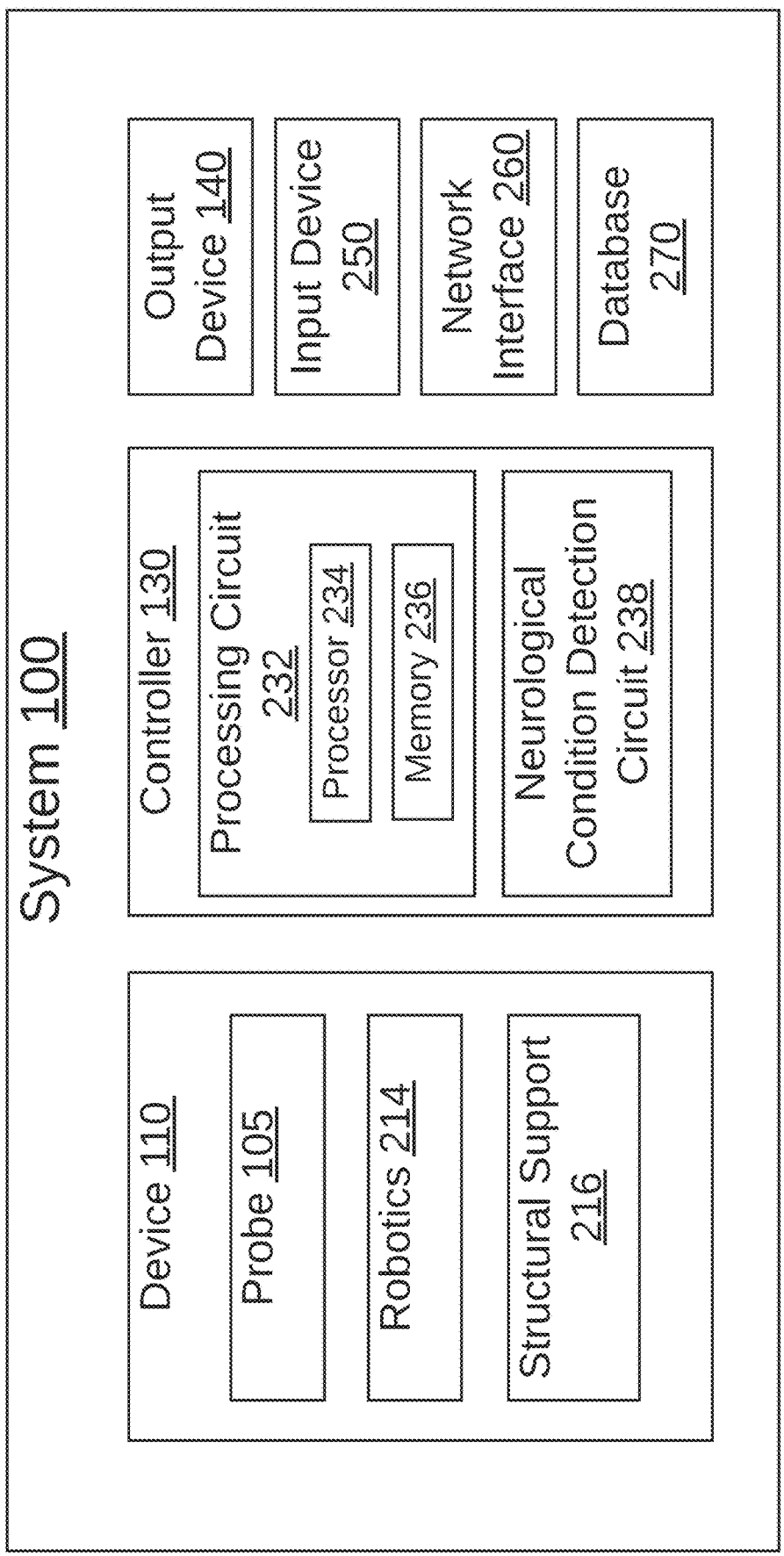
FIG. 2 is a schematic block diagram illustrating the system (FIG. 1) according to various arrangements.

FIG. 2 is a schematic block diagram illustrating the system 100 (FIG. 1) according to various arrangements. Referring to FIGS. 1-2, the device 110 includes the probe 105 as described. Further disclosure regarding examples of the probe 105 that can be used in conjunction with the system 100 described herein can be found in non-provisional patent application Ser. No. 15/399,648, titled ROBOTIC SYSTEMS FOR CONTROL OF AN ULTRASONIC PROBE, and filed on Jan. 5, 2017, which is incorporated herein by reference in its entirety. In some arrangements, the device 110 is configured to automatically or robotically operate the probe 105.

In some arrangements, the device 110 includes robotics 214 configured to control positioning of the probe 105. For example, the robotics 214 are configured to translate the probe 105 along a surface of the head and to move the probe 105 with respect to (e.g., toward and away from) the head along various axes in the Cartesian, spherical, and rotational coordinate systems. In particular, the robotics 214 can include a multiple degree of freedom (DOF) TCD transducer positioning system with motion planning. In some arrangements, the robotics 214 are capable of supporting two, three, four, five, or six DOF movements of the probe 105 with respect to the head. In some instances, the robotics 214 can translate in X and Y axes (e.g., along a surface of the head) to locate a temporal window region in translational axes, and in Z axis with both force and position feedback control to both position and maintain the appropriate force against the skull/skin to maximize signal quality by maintaining appropriate contact force. Two angular DOF (e.g., pan and tilt) may be used to maximize normal insonation of blood vessels to maximize velocity signals.

In some arrangements, an end of the probe 105 is operatively coupled to or otherwise interfaces with the robotics 214. The robotics 214 include components, such as but not limited to a motor assembly and the like for controlling the positioning of the probe 105 (e.g., controlling z-axis pressure, normal alignment, or the like of the probe 105). In some arrangements, the registration of the probe 105 against the head is accomplished using the robotics 214 to properly position and align the probe 105 in the manner described.

In some arrangements, the probe 105 includes a first end and a second end that is opposite to the first end. In some arrangements, the first end includes a concave surface that is configured to be adjacent to or contact a scanning surface on the head. The concave surface is configured with a particular pitch to focus generated energy towards the scanning surface. In some arrangements, the device 110 is a TCD apparatus such that the first end of the probe 105 is configured to be adjacent to or contact and align along a side of the head. The first end of the probe 105 is configured to provide ultrasound wave emissions from the first end and directed into the head (e.g., toward the brain). For example, the first end of the probe 105 can include a transducer (such as, but not limited to, an ultrasound transducer, TCD, transcranial color-coded sonography (TCCS), or acoustic ultrasound transducer array such as sequential arrays or phased arrays) that emits acoustic energy capable of penetrating windows in the skull/head or neck.

In some arrangements, the second end of the probe 105 is coupled to the robotics 214. In some arrangements, the second end of the probe 105 includes a threaded section along a portion of the body of the probe 105. The second end is configured to be secured in the robotics 214 via the threads (e.g., by being screwed into the robotics 214). In other arrangements, the probe 105 is secured in the robotics 214 by any other suitable connecting means, such as but not limited to welding, adhesive, one or more hooks and latches, one or more separate screws, press fittings, or the like.

In other arrangements, the device 110 does not include robotics 214 and the probe 105 is manually operated and moved by a technician such that the second end of the probe 105 is handled by the technician.

The device 110 can further include a structural support 216 configured to support the head of the subject and/or to support the device 110 on the head or other parts of a body of the subject. In some examples, the structural support 216 includes a platform (e.g., a baseplate) that allows the subject to lay down on a flat surface in a reclined or supine position while the device 110 is operational. The structural support 216 can be made from any suitably malleable material that allows for flexing, such as, but not limited to, flexible plastics, polyethylene, urethanes, polypropylene, ABS, nylon, fiber-reinforced silicones, structural foams, or the like.

In some arrangements, the system 100 includes an input device 250. The input device 250 includes any suitable device configured to allow an operator, physician, or care provider personnel to input information or commands into the system 100. In some arrangements, the input device 250 includes but is not limited to, a keyboard, a keypad, a mouse, a joystick, a touchscreen display, a microphone, or any other input device performing a similar function. In some arrangements, the input device 250 and the output device 140 can be a same input/output device (e.g., a touchscreen display device).

In some arrangements, the network interface 260 is structured for sending and receiving data (e.g., results, instructions, requests, software or firmware updates, and the like) over a communication network (e.g., the network 120). Accordingly, the network interface 260 includes any of a cellular transceiver (for cellular standards), local wireless network transceiver (for 802.11X, ZigBee, Bluetooth®, Wi-Fi, or the like), wired network interface, a combination thereof (e.g., both a cellular transceiver and a Bluetooth transceiver), and/or the like. In some examples, the network interface 260 includes any method or device configured to send data from the device 110 to the controller 130. In that regard, the network interface 260 may include Universal Serial Bus (USB), FireWire, serial communication, and the like.

In some arrangements, the input device 250, the output device 140, the network interface 260, and the controller 130 form a single computing system that resides on a same node on the network 120. The device 110 is configured to be connected to the computing system via the network 120. The network interface 260 is configured to communicate data to and from the device 110 via the network 120. In such arrangements, the device 110 includes a similar network interface (not shown) to communicate data to and from the computing device via the network 120. In other arrangements in which the device 110, the controller 130, the output device 140, the input device 250, and the network interface 260 all reside in a same computing device on a same node of a network, the network interface 260 is configured to communicate data with another suitable computing system (e.g., cloud data storage, remote server, and the like).

In some arrangements, the controller 130 is configured for controlling operations, processing data, executing input commands, providing results, and so on. For example, the controller 130 is configured to receive input data or instructions from the input device 250 or the network interface 260, to control the system 100 to execute the commands, to receive data from the device 110, to provide information to the output device 140 or network interface 260, and so on.

The controller 130 includes a processing circuit 232 having a processor 234 and a memory 236. In some arrangements, the processor 234 can be implemented as a general-purpose processor and is coupled to the memory 236. The processor 234 includes any suitable data processing device, such as a microprocessor. In the alternative, the processor 234 includes any suitable electronic processor, controller, microcontroller, or state machine. In some arrangements, the processor 234 is implemented as a combination of computing devices (e.g., a combination of a Digital Signal Processor (DSP) and a microprocessor, a plurality of microprocessors, at least one microprocessor in conjunction with a DSP core, or any other such configuration). In some arrangements, the processor 234 is implemented as an Application Specific Integrated Circuit (ASIC), one or more Field Programmable Gate Arrays (FPGAs), a Digital Signal Processor (DSP), a group of processing components, or other suitable electronic processing components.

In some arrangements, the memory 236 includes a non-transitory processor-readable storage medium that stores processor-executable instructions. In some arrangements, the memory 236 includes any suitable internal or external device for storing software and data. Examples of the memory 236 include but are not limited to, Random Access Memory (RAM), Read-Only Memory (ROM), Non-Volatile RAM (NVRAM), flash memory, floppy disks, hard disks, dongles or other Recomp Sensor Board (RSB)-connected memory devices, or the like. The memory 236 can store an Operating System (OS), user application software, and/or executable instructions. The memory 236 can also store application data, such as an array data structure. In some arrangements, the memory 236 stores data and/or computer code for facilitating the various processes described herein.

As used herein, the term "circuit" can include hardware structured to execute the functions described herein. In some arrangements, each respective circuit can include machine-readable media for configuring the hardware to execute the functions described herein. The circuit can be embodied as one or more circuitry components including, but not limited to, processing circuitry, network interfaces, peripheral devices, input devices, output devices, sensors, etc. In some arrangements, a circuit can take the form of one or more analog circuits, electronic circuits (e.g., integrated circuits (IC), discrete circuits, system on a chip (SOCs) circuits, etc.), telecommunication circuits, hybrid circuits, and any other suitable type of circuit. In this regard, the circuit can include any type of component for accomplishing or facilitating achievement of the operations described herein. For example, a circuit as described herein can include one or more transistors, logic gates (e.g., NAND, AND, NOR, OR, XOR, NOT, XNOR, etc.), resistors, multiplexers, registers, capacitors, inductors, diodes, wiring, and so on.

The circuit can also include one or more processors communicatively coupled to one or more memory or memory devices. In this regard, the one or more processors can execute instructions stored in the memory or can execute instructions otherwise accessible to the one or more processors. In some arrangements, the one or more processors can be embodied in various ways. The one or more processors can be constructed in a manner sufficient to perform at least the operations described herein. In some arrangements, the one or more processors can be shared by multiple circuits (e.g., a first circuit and a second circuit can comprise or otherwise share the same processor which, in some example arrangements, can execute instructions stored, or otherwise accessed, via different areas of memory). Alternatively, or additionally, the one or more processors can be structured to perform or otherwise execute certain operations independent of one or more co-processors. In other example arrangements, two or more processors can be coupled via a bus to enable independent, parallel, pipelined, or multi-threaded instruction execution. Each processor can be implemented as one or more general-purpose processors, ASICs, FPGAs, DSPs, or other suitable electronic data processing components structured to execute instructions provided by memory. The one or more processors can take the form of a single core processor, multi-core processor (e.g., a dual core processor, triple core processor, quad core processor, etc.), microprocessor, etc. In some arrangements, the one or more processors can be external to the apparatus, for example, the one or more processors can be a remote processor (e.g., a cloud-based processor). Alternatively, or additionally, the one or more processors can be internal and/or local to the apparatus. In this regard, a given circuit or components thereof can be disposed locally (e.g., as part of a local server, a local computing system, etc.) or remotely (e.g., as part of a remote server such as a cloud-based server). To that end, a circuit, as described herein can include components that are distributed across one or more locations.

An example system for implementing the overall system or portions of the arrangements can include a general-purpose computer, including a processing unit, a system memory, and a system bus that couples various system components including the system memory to the processing unit. Each memory device can include non-transient volatile storage media, non-volatile storage media, non-transitory storage media (e.g., one or more volatile and/or non-volatile memories), etc. In some arrangements, the non-volatile media may take the form of ROM, flash memory (e.g., flash memory such as NAND, 3D NAND, NOR, 3D NOR, etc.), Electrically Erasable Programmable Read-Only Memory (EEPROM), Magnetoresistive Random Access Memory (MRAM), magnetic storage, hard discs, optical discs, etc. In other arrangements, the volatile storage media can take the form of RAM, Thyristor Random Access Memory (TRAM), Z-Capacitor Random Access Memory (ZRAM), etc. Combinations of the above are also included within the scope of machine-readable media. In this regard, machine-executable instructions comprise, for example, instructions and data which cause a general-purpose computer, special purpose computer, or special purpose processing machines to perform a certain function or group of functions. Each respective memory device can be operable to maintain or otherwise store information relating to the operations performed by one or more associated circuits, including processor instructions and related data (e.g., database components, object code components, script components, etc.), in accordance with the example arrangements described herein.

The controller 130 further includes a neurological condition detection circuit 238, which can be implemented with the processing circuit 232 or another dedicated processing circuit. In some examples, the neurological condition detection circuit 238 can be implemented with two or more circuits. The neurological condition detection circuit 238 receives the ultrasound data from the device 110 and determines presence of a neurological condition based on the ultrasound data, as described herein.

In some arrangements, ultrasound scans are acquired by a technician using a hand-held ultrasound probe 105 and a manual device 110 (e.g., robotics 214 are not involved). In other arrangements, the device 110 is automated and includes the robotics 214. Ultrasound data (e.g., CBFV signals) associated with one or more blood vessels (e.g., the left and right middle cerebral arteries (MCA)) in the head of the subject are identified via insonation through and acoustic window at the head of the subject (e.g., the transtemporal window). In some arrangements, CBFV envelopes are digitally sampled by the detection circuit 238 at a sampling rate (e.g., 125 Hz) and recorded throughout the entire exam. Once the CBFV signal was identified and optimized at a specific depth by the detection circuit 238 (or manually), waveform recordings can then be made in intervals (e.g., 30-second intervals). In some arrangements, the device 110 obtains recordings for as many depths as possible (e.g., between 45-60 millimeters). For example, the recordings are obtained in both the left/right cerebral hemispheres. In other arrangements, recordings are obtained at only one hemisphere at a time or for just one hemisphere only.

In some arrangements, ultrasound data of other portions of the brain are collected. For example, other arteries within the brain are insonated so that the methods described herein are performed. Other arteries include, but are not limited to, MCA, interior carotid artery, anterior cerebral artery, posterior communicating artery, posterior cerebral artery, ophthalmic artery, and other arteries within the brain (e.g., within the circle of Willis).

In some arrangements, average beat waveforms from each recorded depth interval are extracted (e.g., using an automated beat identification algorithm and/or manual checking/editing). Detected beats which lacked clear pulsatile structure and/or deviated anomalously from the group average (e.g., usually due to probe displacement during recording), can be excluded. In some arrangements, the detection circuit 238 aligns and averages the remaining beats, resulting in a single representative beat waveform for each recorded depth interval.

In some arrangements, since Doppler velocities scale with the cosine of the incident angle between the ultrasound beam and underlying blood flow, waveforms for a given vessel with the highest measured velocities are assumed to most accurately reflect reality. As such, in some arrangements, for a subject, a single bilateral (left/right) pair of average beat waveforms for analysis consisting of those with maximal mean velocity across all recorded depths for each hemisphere can be selected. In other arrangements, the beat waveform is unilateral from only one side of the head.

In some arrangements, from the collected and processed data, a curvature metric can be calculated by the neurological condition detection circuit 238. Curvature is a well-defined mathematical property of space curves which quantifies the degree to which a curve deviates from being "straight" at a given point. In some arrangements, the curvature metric specific to TCD quantifies the degree to which a beat is blunted and/or dampened. In some arrangements, since curvature is a nonlinear function sensitive to small inflections associated with high frequency noise, the neurological condition detection circuit 238 first smooths the average beat waveform (e.g., via convolution with a Hanning window, for example, 9 ms). Moreover, in some arrangements, the detection circuit 238 considers curvature associated with the beat systolic complex, where the signal-to-noise ratio is presumably greatest. The systolic complex, or "beat canopy," comprises the proportion of the beat with the highest velocities and richest morphological structure.

In some arrangements, to compute a curvature metric for a given TCD beat waveform, curvature is first computed for each time point ($t_i$) of the smoothed beat (denoted $x(t_i)$ below) via the discretized equation for graph curvature (equation 1) expressed in terms of finite differences. $\Delta$ and $\delta^2$ in equation 1 denote the first order forward (equation 2) and second order central (equation 3) finite difference equations. In some arrangements, the curvature metric, defined by equation 5, is computed as the sum of curvature taken over all individual time points comprising the beat canopy (C). The beat canopy is defined in equation 4 as the set of time points wherein velocity exceeds one quarter of its total diastolic-systolic range ($t_d$, and $t_s$ denoting the time points corresponding to diastolic minimum and systolic max, respectively). Since the hypothesized effect of occlusion on the TCD waveform is to lower curvature in the occluded vessel, when assessing a bilateral pair of waveforms the curvature metric can be taken as the minimum computed for each member of the pair. In some arrangements, the curvature metric is a positive metric.

$$k(t_i) = \frac{|\delta^2[x](t_i)|}{\left(1 + (\Delta[x](t_i))^2\right)^{\frac{3}{2}}} \quad (1)$$

$$\Delta[x](t_i) = x(t_{i+1}) - x(t_i) \quad (2)$$

$$\delta^2[x](t_i) = x(t_{i+1}) - 2x(t_i) + x(t_{i-1}) \quad (3)$$

$$C = \left\{ i : x(t_i) \geq x(t_d) + \frac{x(t_s) - x(t_d)}{4} \right\} \quad (4)$$

$$VCI = \sum_{i \in C} k(t_i) \quad (5)$$

In some arrangements, from the collected and processed data, a velocity asymmetry metric can be calculated by the neurological condition detection circuit 238. Velocity asymmetry is a metric which quantifies the degree to which average CBFV observed for a vessel in a given cerebral hemisphere differs from that observed in the corresponding vessel in the opposite hemisphere. Accordingly, CBFV in an occluded vessel may be lower than that of the corresponding unaffected hemisphere. In some arrangements, for a bilateral pair of left/right average beat waveforms, denoted $x_L(t)$ (with $N_L$ total time points), and $x_R(t)$ (with $N_R$ time points) in equations 6 and 7, respectively, the velocity asymmetry metric (defined in equation 8) is computed as the minimum average velocity across hemispheres divided by the corresponding maximum. Accordingly, in some arrangements, the velocity asymmetry metric is a positive definite metric bounded on the closed interval [0, 1].

$$\mu_L = \frac{1}{N_L} \sum_{i=1}^{N_L} x_L(t_i) \quad (6)$$

$$\mu_R = \frac{1}{N_R} \sum_{i=1}^{N_R} x_R(t_i) \quad (7)$$

$$VAI = \frac{\min(\{\mu_L, \mu_R\})}{\max(\{\mu_L, \mu_R\})} \quad (8)$$

Figure 3:
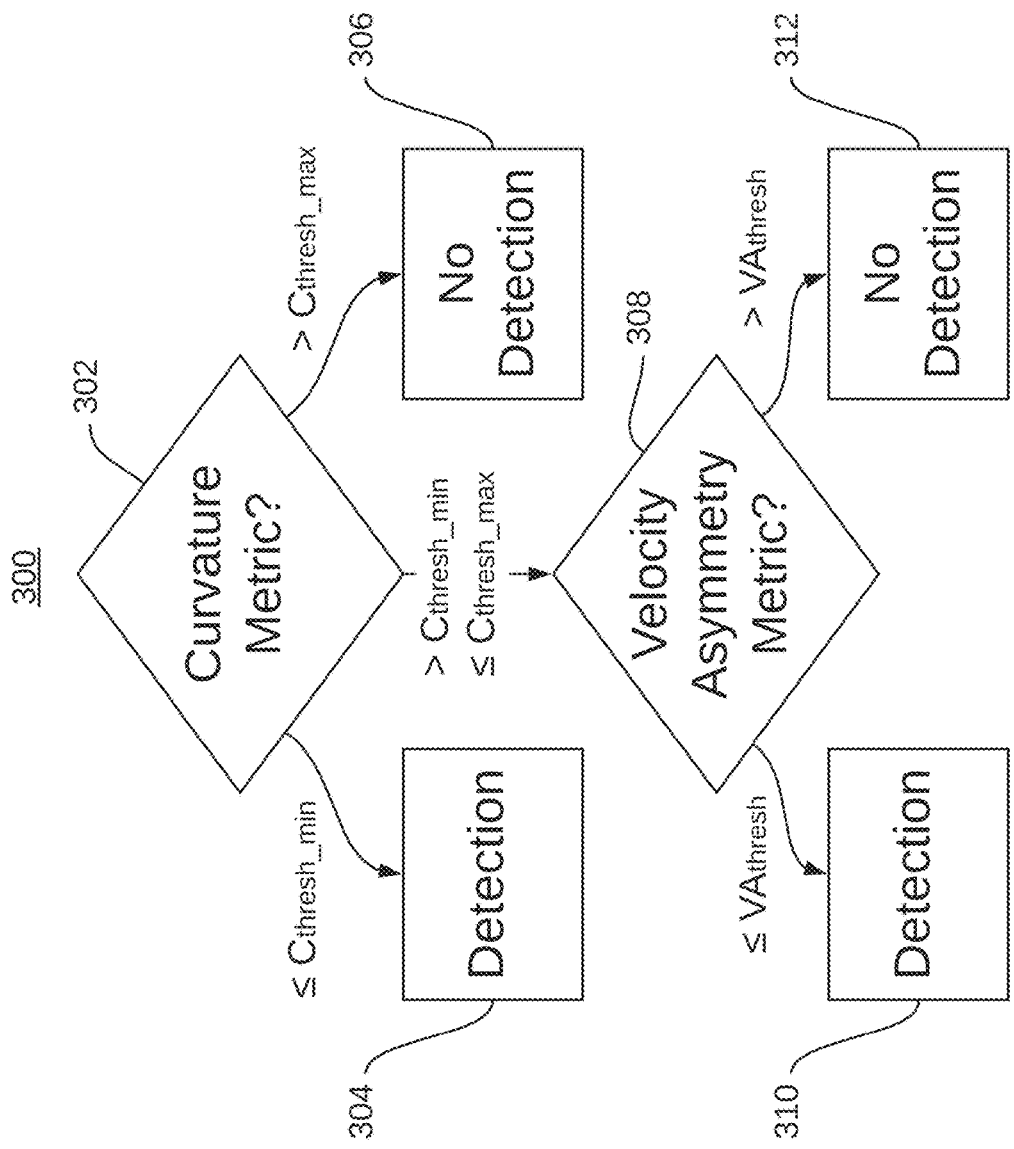
FIG. 3 is a decision tree diagram illustrating a method for detecting neurological conditions using the system (FIG. 1) according to various arrangements.

FIG. 3 is a decision tree diagram 300 illustrating a method for detecting neurological conditions using the system (FIG. 1) according to various arrangements.

In some arrangements, the curvature metric and the velocity asymmetry metric are combined into a single classifier using simple and intuitive decision criteria. The approach includes augmenting the curvature assessment such that subjects with curvature less than some low critical threshold are classified as having the neurological condition (e.g., LVO), whereas curvature exceeding some high critical threshold are classified as not having the neurological condition. However, a curvature metric observed to fall between these thresholds are deemed uncertain and decided then based on velocity asymmetry.

Accordingly, referring to FIG. 3, in some arrangements, the decision tree diagram 300 includes determining the curvature metric at step 302, as described above. The curvature metric is compared to a minimum curvature threshold, and if the curvature metric is below (or equal to or below) the minimum curvature threshold, the neurological condition can be deemed as detected by the neurological condition detection circuit 238 (at step 304). Furthermore, the curvature metric is compared to a maximum curvature threshold (e.g., if step 304 is deemed to not be reached because the curvature metric is above the minimum curvature threshold), and if the curvature metric is above (or equal to or above) the maximum curvature threshold, the neurological condition can be deemed as not detected by the neurological condition detection circuit 238 (at step 306).

In some arrangements, if the neurological condition detection circuit 238 determines that the curvature metric is between the minimum curvature threshold and the maximum curvature threshold, then the velocity asymmetry metric is used to determine presence of the neurological condition (at step 308). For example, the velocity asymmetry metric is compared to a velocity asymmetry threshold, and if the velocity asymmetry metric is below (or equal to or below) the velocity asymmetry threshold, the neurological condition can be deemed as detected by the neurological condition detection circuit 238 (at step 310). Furthermore, if the velocity asymmetry metric is above (or equal to or above) the velocity asymmetry threshold, the neurological condition can be deemed as not detected by the neurological condition detection circuit 238 (at step 312).

In some arrangements, the various thresholds described can be adjustable. For example, due to the clinical preference for finding true positives at the expense of true negatives, the thresholds can be adjusted to over diagnose the neurological condition, rather than missing out on potential true detections that should have been made. Similarly, the thresholds can be adjusted the opposite way such that less false positive detections are made. In some arrangements, the thresholds are adjusted based on the particular subject. For example, the thresholds can be adjusted based on one or more of the race, gender, body composition, age, and so on of the subject.

Figure 4A:
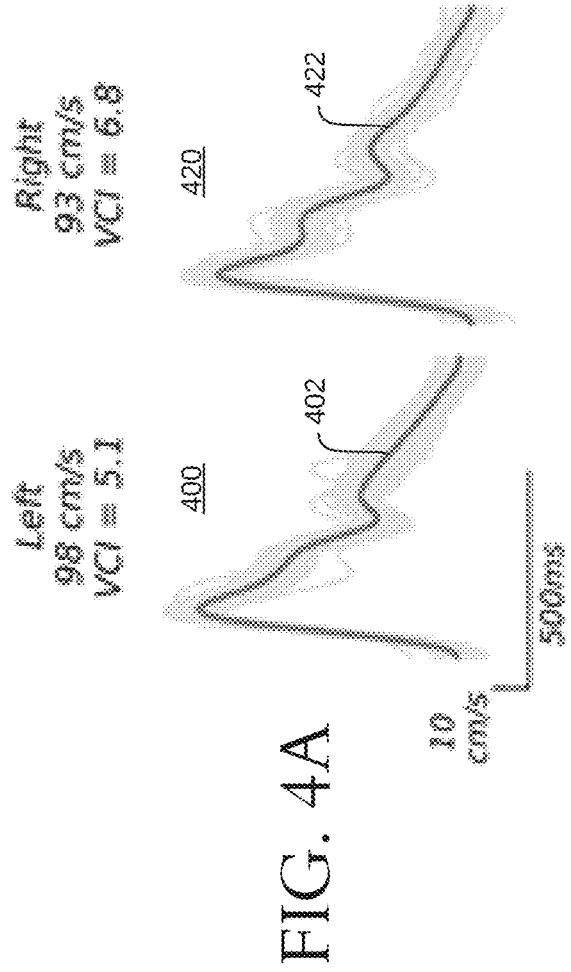
FIG. 4A is a graph illustrating waveforms depicting ultrasound data from a healthy subject according to various arrangements.
Figure 4B:
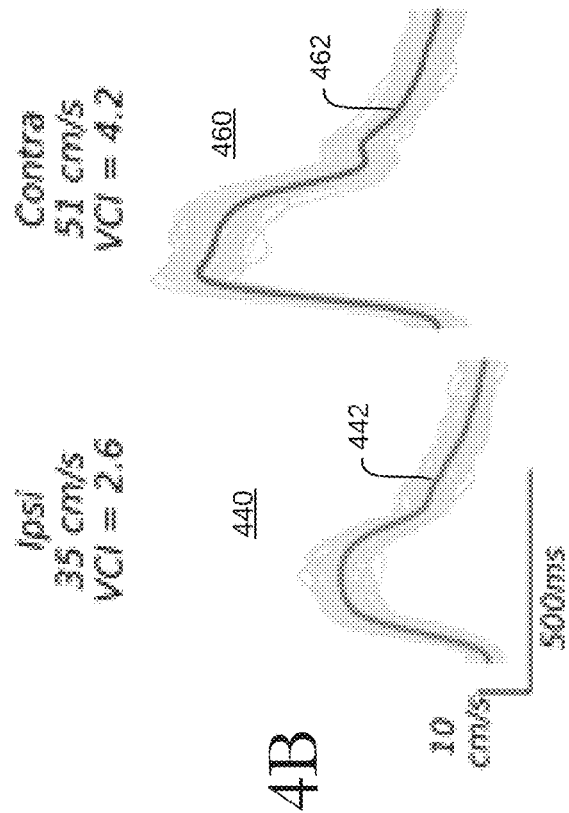
FIG. 4B is a graph illustrating waveforms depicting ultrasound data from a subject having a neurological condition according to various arrangements.

FIG. 4A is a graph illustrating waveforms depicting ultrasound data from a subject according to various arrangements. FIG. 4B is a graph illustrating waveforms depicting ultrasound data from a subject according to various arrangements.

Referring to FIGS. 4A and 4B, a graph 400 is depicted including an average waveform 402 that is derived from an individual beat ensemble (the shadow waveforms surrounding the average waveform 402). Similarly, graphs 420, 440, and 460 including average waveforms 422, 442, and 462, respectively, derived from their corresponding individual beat ensembles, are shown. Graphs 400 and 420 illustrate respective waveforms from different parts of an anatomy of a subject. For example, graph 400 depicts a waveform from one portion of the brain at one hemisphere and graph 420 depicts a waveform from a different portion of the brain at the opposite hemisphere. In some arrangements, the waveform 402 depicts the MCA from the left hemisphere of the brain and the waveform 422 depicts the MCA from the right hemisphere. Similarly, graphs 440 and 460 can depict waveforms from opposite hemispheres of the subject's brain.

In some arrangements, the graphs 400 and 420 depict a subject that does not have a detected neurological condition. As such, the waveforms 402 and 422 display high curvature metrics in both hemispheres, and relatively symmetric bilateral velocities (e.g., velocity asymmetry metric of 0.95).

In some arrangements, the graphs 440 and 460 depict a subject that does have a detected neurological condition (e.g., LVO). For example, the waveform 442 depicts a decreased curvature metric, which is especially pronounced in the ipsilateral hemisphere (same side as the occlusion), as well as less symmetric velocity (e.g., velocity asymmetry metric of 0.69).

In some arrangements, the graphs 400, 420, 440, or 460 (and the related information shown) are displayed on an output device of the system 100 (e.g., at the output device 140). In other arrangements, the curvature metric and/or the velocity asymmetry metric is displayed in different suitable ways, such as, but not limited to, a percentage or other value from 0 to 100 indicating the lowest curvature or velocity asymmetry metric value to the highest curvature or velocity asymmetry metric value, respectively, a dial indicating the value of the curvature or velocity asymmetry matric, a meter, and so on. In some arrangements, this visualization at a display indicating a current curvature or velocity asymmetry metric can be updated in real time as the robotic or manual probe 105 is operated at the subject.

In some arrangements, the detection of the neurological condition itself is displayed at the output device 140. For example, the output device 140 can display a YES or a NO corresponding to whether or not the subject has the neurological condition. In some arrangements, the output device 140 can display a confidence level in the diagnosis (e.g., if the curvature metric is far above the maximum curvature threshold, then the confidence level can be high, but if the curvature metric is found to be between the minimum curvature threshold and the maximum curvature threshold, then the confidence level can be less). As an example, the confidence level can be displayed as a percentage from 0 to 100 from lowest to highest, respectively.

In some arrangements, rather than the output device 140 displaying the graphs 400, 420, 440, and 460 side-by-side, the output device 140 superimposes the corresponding graphs on top of each other so that a health care provider can easily determine the differences in velocity and curvature at the different sections of the subject's head that were collected.

The above used terms, including "held fast," "mount," "attached," "coupled," "affixed," "connected," "secured," and the like are used interchangeably. In addition, while certain arrangements have been described to include a first element as being "coupled" (or "attached," "connected," "fastened," etc.) to a second element, the first element may be directly coupled to the second element or may be indirectly coupled to the second element via a third element.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. All structural and functional equivalents to the elements of the various aspects described throughout the previous description that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed as a means plus function unless the element is expressly recited using the phrase "means for."

It is understood that the specific order or hierarchy of steps in the processes disclosed is an example of illustrative approaches. Based upon design preferences, it is understood that the specific order or hierarchy of steps in the processes may be rearranged while remaining within the scope of the previous description. The accompanying method claims present elements of the various steps in a sample order, and are not meant to be limited to the specific order or hierarchy presented.

The previous description of the disclosed implementations is provided to enable any person skilled in the art to make or use the disclosed subject matter. Various modifications to these implementations will be readily apparent to those skilled in the art, and the generic principles defined herein may be applied to other implementations without departing from the spirit or scope of the previous description. Thus, the previous description is not intended to be limited to the implementations shown herein but is to be accorded the widest scope consistent with the principles and novel features disclosed herein.

The various examples illustrated and described are provided merely as examples to illustrate various features of the claims. However, features shown and described with respect to any given example are not necessarily limited to the associated example and may be used or combined with other examples that are shown and described. Further, the claims are not intended to be limited by any one example.

The foregoing method descriptions and the process flow diagrams are provided merely as illustrative examples and are not intended to require or imply that the steps of various examples must be performed in the order presented. As will be appreciated by one of skill in the art the order of steps in the foregoing examples may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm steps described in connection with the examples disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The preceding description of the disclosed examples is provided to enable any person skilled in the art to make or use the present disclosure. Various modifications to these examples will be readily apparent to those skilled in the art, and the generic principles defined herein may be applied to some examples without departing from the spirit or scope of the disclosure. Thus, the present disclosure is not intended to be limited to the examples shown herein but is to be accorded the widest scope consistent with the following claims and the principles and novel features disclosed herein.

It should be noted that although the diagrams herein may show a specific order and composition of method blocks, it is understood that the order of these blocks may differ from what is depicted. For example, two or more blocks may be performed concurrently or with partial concurrence. Also, some method blocks that are performed as discrete blocks may be combined, blocks being performed as a combined block may be separated into discrete blocks, the sequence of certain processes may be reversed or otherwise varied, and the nature or number of discrete processes may be altered or varied. The order or sequence of any element or apparatus may be varied or substituted according to alternative arrangements. Accordingly, all such modifications are intended to be included within the scope of the present disclosure as defined in the appended claims. Such variations will depend on the machine-readable media and hardware systems chosen and on designer choice. It is understood that all such variations are within the scope of the disclosure. Likewise, software and web arrangements of the present disclosure could be accomplished with standard programming techniques with rule based logic and other logic to accomplish the various database searching blocks, correlation blocks, comparison blocks, and decision blocks.

What is claimed is:

1. A tool for determining presence or absence of a neurological condition in a subject, comprising:
    an ultrasound device configured to collect ultrasound data from a head of the subject;
    a processing circuit configured to:
        determine a curvature metric based on the ultrasound data;
        determine uncertainty in identifying the presence or the absence of the neurological condition in the subject based on the curvature metric;
        in response to determining the uncertainty, determine a velocity asymmetry metric based on the ultrasound data to address the uncertainty; and
        in response to determining the velocity asymmetry metric, determine the presence or the absence of the neurological condition in the subject based on the velocity asymmetry metric.

2. The tool in claim 1, wherein determining the uncertainty in identifying the presence or the absence of the neurological condition in the subject based on the curvature metric comprises determining that the curvature metric is between a minimum curvature threshold and a maximum curvature threshold.

3. The tool in claim 2, wherein one or more of the minimum curvature threshold or the maximum curvature threshold are configured to be increased or decreased by an operator of the tool.

4. The tool in claim 2, wherein in response to determining the uncertainty, determining the velocity asymmetry metric based on the ultrasound data comprises in response to determining that determining that the curvature metric is between the minimum curvature threshold and the maximum curvature threshold, comparing the velocity asymmetry metric to a velocity asymmetry threshold.

5. The tool of claim 4, wherein, in response to determining that the velocity asymmetry metric is less than the velocity asymmetry threshold, the processing circuit is configured to determine the presence of the neurological condition.

6. The tool of claim 4, wherein, in response to determining that the velocity asymmetry metric is greater than the velocity asymmetry threshold, the processing circuit is configured to determine absence of the neurological condition.

7. The tool of claim 1, wherein the ultrasound data comprises a first blood flow waveform from a first anatomical portion of the head of the subject and a second blood flow waveform from a second anatomical portion of the head of the subject, the first anatomical portion different from the second anatomical portion.

8. The tool of claim 7, wherein the first anatomical portion comprises a first blood vessel of the head of the subject and the second anatomical portion comprises a second blood vessel of the head of the subject.

9. The tool of claim 8, wherein the first blood vessel comprises a right middle cerebral artery of the subject and the second blood vessel comprises a left middle cerebral artery of the subject.

10. The tool of claim 1, wherein the neurological condition comprises Large Vessel Occlusion.

11. The tool of claim 1, wherein
    the tool further comprises or is operatively coupled to a display; and
    the processing circuit is further configured to cause the display to show one or more indicators at the display representing the calculated curvature metric and the velocity asymmetry metric.

12. A method for determining presence or absence of a neurological condition in a subject, comprising:
    determining a curvature metric based on ultrasound data collected from a head of the subject;
    determining uncertainty in identifying the presence or the absence of the neurological condition in the subject based on the curvature metric;
    in response to determining the uncertainty, determining a velocity asymmetry metric based on the ultrasound data to address the uncertainty; and
    in response to determining the velocity asymmetry metric, determining the presence or the absence of the neurological condition in the subject based on the velocity asymmetry metric.

13. At least one non-transitory processor-readable medium storing processor-readable instructions such that, when executed, causes a processor to determine presence or absence of a neurological condition by:

determining a curvature metric based on ultrasound data collected from a head of the subject;

determining uncertainty in identifying the presence or the absence of the neurological condition in the subject based on the curvature metric;

in response to determining the uncertainty, determining a velocity asymmetry metric based on the ultrasound data to address the uncertainty; and in response to determining the velocity asymmetry metric, determining the presence or the absence of the neurological condition in the subject based on the velocity asymmetry metric.

14. The non-transitory processor-readable medium in claim 13, wherein determining the uncertainty in identifying the presence or the absence of the neurological condition in the subject based on the curvature metric comprises determining that the curvature metric is between a minimum curvature threshold and a maximum curvature threshold.

15. The non-transitory processor-readable medium in claim 14, wherein one or more of the minimum curvature threshold or the maximum curvature threshold are configured to be increased or decreased by an operator of the tool.

16. The non-transitory processor-readable medium in claim 15, wherein in response to determining the uncertainty, determining the velocity asymmetry metric based on the ultrasound data comprises in response to determining that determining that the curvature metric is between the minimum curvature threshold and the maximum curvature threshold, comparing the velocity asymmetry metric to a velocity asymmetry threshold.

17. The non-transitory processor-readable medium of claim 16, wherein, in response to determining that the velocity asymmetry metric is less than the velocity asymmetry threshold, the processing circuit is configured to determine the presence of the neurological condition.

18. The non-transitory processor-readable medium of claim 16, wherein, in response to determining that the velocity asymmetry metric is greater than the velocity asymmetry threshold, the processing circuit is configured to determine absence of the neurological condition.

19. The non-transitory processor-readable medium of claim 13, wherein the ultrasound data comprises a first blood flow waveform from a first anatomical portion of the head of the subject and a second blood flow waveform from a second anatomical portion of the head of the subject, the first anatomical portion different from the second anatomical portion.

20. The non-transitory processor-readable medium of claim 13, wherein the neurological condition comprises Large Vessel Occlusion.

* * * * *